(12) United States Patent
Novitski et al.

(10) Patent No.: US 10,851,038 B1
(45) Date of Patent: Dec. 1, 2020

(54) ULTRASONIC CANNABINOID EXTRACTION USING NON-FLAMMABLE CO-SOLVENT

(71) Applicant: Nextleaf Solutions Ltd., Coquitlam (CA)

(72) Inventors: David Michael Novitski, Burnaby (CA); Xuan Jia, Burnaby (CA)

(73) Assignee: Nextleaf Solutions Ltd., Vancouver (CA)

( * ) Notice: Subject to any disclaimer, the term of this patent is extended or adjusted under 35 U.S.C. 154(b) by 0 days.

(21) Appl. No.: 16/716,197

(22) Filed: Dec. 16, 2019

(51) Int. Cl.
*A61K 36/00* (2006.01)
*C07C 37/00* (2006.01)
*C07D 311/80* (2006.01)

(52) U.S. Cl.
CPC .......... *C07C 37/004* (2013.01); *C07D 311/80* (2013.01)

(58) Field of Classification Search
CPC ...................................................... A61K 36/00
USPC ............................................................ 424/725
See application file for complete search history.

(56) References Cited

U.S. PATENT DOCUMENTS

2012/0237466 A1* 9/2012 Graham .................. A61Q 5/06
424/60

* cited by examiner

*Primary Examiner* — Michael V Meller
(74) *Attorney, Agent, or Firm* — Damien G. Loveland

(57) ABSTRACT

A slurry is made with ground cannabis biomass and a non-flammable co-solvent. The non-flammable co-solvent is made up of water and ethanol. The ultrasonication process extracts cannabinoids by applying ultrasound to the slurry. The slurry is then filtered, optionally centrifuged, and then distilled to obtain cannabinoid oil.

8 Claims, 2 Drawing Sheets

ULTRASONIC CANNABINOID EXTRACTION USING NON-FLAMMABLE CO-SOLVENT

TECHNICAL FIELD

Cannabinoid molecules such as tetrahydrocannabinol (THC) and/or cannabidiol (CBD) are extracted from cannabis biomass via an ultrasonication process. More specifically, the process involves a non-flammable co-solvent for the cannabinoid extraction.

BACKGROUND

The recent legalization of cannabis for recreational use in several parts of the world is responsible for the expansion of the cannabis industry. Making new products for this industry is important for developing the market. However, these new products must be made in agreement with safety standards established by local governments.

Most of the currently used techniques for cannabinoid extraction involve solvents that are potentially hazardous for the user. Generally, cannabis extraction involves the use of solvents that are either hazardous, such as butane and ethanol, or expensive such as $CO_2$.

This background is not intended, nor should be construed, to constitute prior art against the present invention.

SUMMARY OF INVENTION

A process is described to extract cannabinoids from cannabis biomass using ultrasound. The process involves the use of hazard-free and non-flammable solvents such as a non-flammable mixture of water and ethanol. The ultrasound is applied using an ultrasonication apparatus. Moreover, the process is run continuously but can also be run in batches.

Disclosed herein is a process for extracting cannabinoids from cannabis biomass comprising mixing a non-flammable co-solvent with the cannabis biomass to form a slurry; applying ultrasound to the slurry to extract cannabinoids from the cannabis biomass into the co-solvent; and then filtering the slurry to remove solid particles from the slurry to form a filtered mixture.

BRIEF DESCRIPTION OF THE DRAWINGS

The following drawings illustrate embodiments of the invention, which should not be construed as restricting the scope of the invention in any way.

DESCRIPTION

A. Glossary

The term "cannabinoids" may refer to a group of chemicals that act on cannabinoid receptors in the body, numerous of which are found in the cannabis plant.

Cannabidiol (CBD) refers to a phytocannabinoid molecule that is obtained, through a decarboxylation process, from the cannabidiolic acid (CBDA) found in cannabis plants.

THC or tetrahydrocannabinol refers to a phytocannabinoid molecule that is found in the cannabis plant mostly in its acidic form, tetrahydrocannabinolic acid (THCA). THCA is the acidic form and precursor to THC. THCA converts to THC via decarboxylation when exposed to heat or sunlight. THC levels in cannabis plants are typically very low, e.g. <2%. THC is known for its psychoactive effect when consumed or inhaled. It is more correctly known as delta-9-tetrahydrocannabinol.

B. Overview

Figure 1:
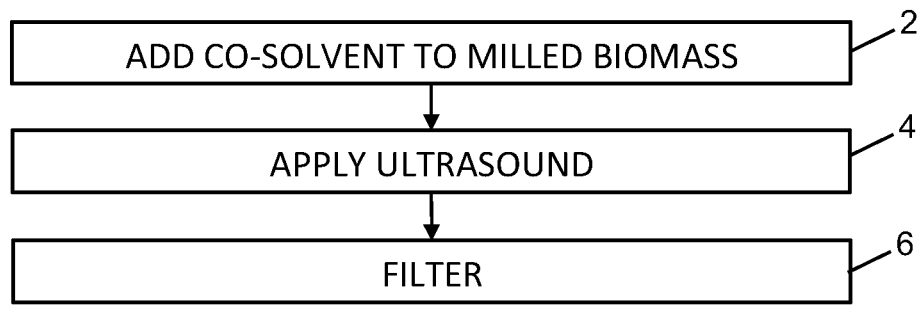
FIG. 1 is a high-level flowchart describing the process for extracting cannabinoids from cannabis biomass according to an embodiment of the present invention.

Referring to FIG. 1, in step 2, a non-flammable co-solvent that is a mix of water and ethanol is added to milled cannabis biomass to form a slurry. The non-flammable co-solvent has a flash point above the highest temperature to which the slurry is expected to rise. In step 4, ultrasound is applied to the slurry in order to extract the cannabinoids from the slurry. Then, in step 6, the slurry is filtered to remove the solid particles from the slurry.

C. Exemplary Process

Figure 2:
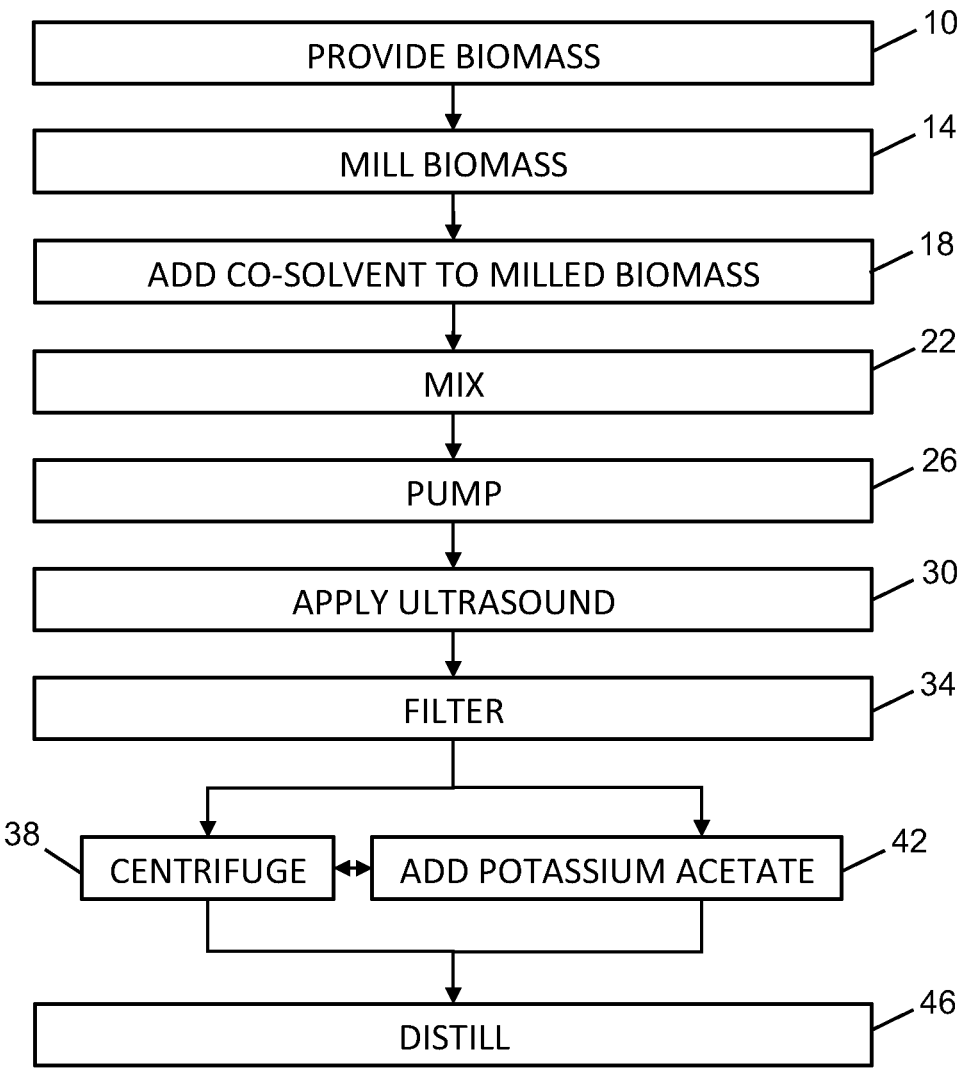
FIG. 2 is a detailed flowchart describing the process for extracting cannabinoids from cannabis biomass according to an embodiment of the present invention.

Referring to FIG. 2, in step 10, cannabis biomass or raw cannabis plant material is provided. Cannabis biomass includes, for example, the flower, the leaves and the stems close to the leaves. Any part of the plant that contains cannabinoid resin glands can be included.

Cannabis biomass is milled using a milling machine in step 14. In some embodiments, cannabis biomass is milled to a particle size of 2 mm or below. In some embodiments, cannabis biomass is milled to a different particle size.

In step 18, a co-solvent is added to the milled cannabis biomass. The ratio of co-solvent to biomass is, for example, in the range of 7:1 to 20:1 by weight, the requirement being that the resulting slurry is flowable. The co-solvent is composed of 97% water and 3% ethanol by volume, for example. The mixing ratio of the co-solvent is chosen to maximize the solubility of the cannabinoids in the co-solvent while keeping the co-solvent non-flammable. In some embodiments, the co-solvent is made up of 95% water and 5% ethanol by volume. In some embodiments, a different mixing ratio of the co-solvent is used as long as the resulting co-solvent is non-flammable. For example, the ratio is such that the flash point of the co-solvent is 62° C. or above. In some embodiments, the composition of the co-solvent is different and involves solvents other than water and/or ethanol that combine to make a non-flammable co-solvent.

In step 22, the milled cannabis biomass is mixed with the co-solvent to form a slurry.

In step 26, the slurry is pumped into a flow-through ultrasonication apparatus or other ultrasonication apparatus via a pump. In other embodiments, the ultrasonication apparatus includes a probe tip (i.e. horn) that is inserted into an open container of the slurry. The slurry is pumped through the ultrasonication apparatus at a low enough rate to receive adequate ultrasound energy from the ultrasonication apparatus when set at a particular power density. The speed of the pump is adjusted to expose the slurry to enough ultrasonication energy in order to extract cannabinoids. The speed of the pump is characterized by the volume of the solute/solvent combination or slurry flowing through per minute. If the speed of the pump is too fast, the efficiency of the cannabinoid extraction decreases. If the speed of the pump is too slow, there is a risk of degrading the product or being less time efficient than other types of extraction.

In some embodiments, the speed of the pump is adjusted in regards to the desired consistency of the final product. The speed of the pump is also adjusted to improve the efficiency and the overall speed of the process.

The ratio of milled cannabis biomass to co-solvent in the slurry is also dependent on the pump diameters and specifications. This is because the slurry must be able to be pumped and flow adequately in the system. In step 30, the ultrasonication process is applied to the slurry. The ultrasonication energy applied to the slurry facilitates the separation of the trichomes from cannabis biomass, facilitates the rupture of the trichomes and/or facilitates the dissolution of the cannabinoids into the co-solvent. The ultrasonication energy is applied to the slurry either continuously or intermittently using a continuous or intermittent vibration profile of the ultrasonication apparatus, which encourages the cannabinoids and/or trichomes from the slurry to enter the co-solvent.

Ultrasound creates small vapor-filled cavities or bubbles in the slurry. When applied continuously, these bubbles break up the cannabis plant material. This facilitates the release of targeted molecules such as cannabinoids into the liquid phase. This phenomenon is modulated by controlling the frequency and/or power of the applied ultrasound.

In step 34, the slurry is then filtered in order to remove solid particles of cannabis biomass from the slurry to form a filtered mixture. In some embodiments, the filtration is implemented directly in the fluid stream from the flow-through cell unit of the ultrasonication apparatus. During step 34, most of the bulk of the cannabis biomass is removed. The filtered mixture contains cannabinoid solute and the co-solvent, and a generally small quantity of finer solid particulates.

After the filtration step 34 there are several different options. In a first option, in step 38, the filtered mixture is processed through a centrifuge. During step 38, the cannabinoids are separated from the co-solvent by centrifugation. In some embodiments, the centrifuge is a bulk or batch centrifuge. In some embodiments, a tubular, disk-type or basket centrifuge is used for the process. When using a bulk or a batch centrifuge, the remaining solid parts of cannabis biomass, or resulting pellets, are separated and removed from the filtered mixture. In some embodiments, a continuous flow centrifuge is used in order to continuously process the filtered mixture. A continuous or batch centrifugation process separates the fine particles of cannabis biomass from the filtered mixture.

During the centrifugation process, the liquid from the filtered mixture with the highest density moves toward the outside of the centrifuge, while the liquid from the filtered mixture with the lower density moves to the center of rotation of the centrifuge. In some embodiments, the water and ethanol co-solvent is the densest liquid in the filtered mixture and therefore moves outwards. The remaining solid parts are removed with the co-solvent as these particles move toward the outside of the centrifuge during the centrifugation step. The inner liquid layer is the lighter, crude oil, which carries the cannabinoids, and it is this layer that is retained as the intermediate product for further processing. In other embodiments, the crude oil has a density that is greater than that of the water and ethanol co-solvent, in which case, the ordering of the layers after centrifuging is different.

In a second option, the filtered mixture from the filtration step 34 is retained for further processing. Potassium acetate is then added to the retained filtered mixture in step 42, to break the ethanol-water azeotrope, and to increase the efficiency of the subsequent centrifugation step 38. Potassium acetate breaks the azeotrope by dissolving in the water and modifying the volatility of the water. The concentration of the potassium acetate used is, for example, 0.06 mol/L, but may in other embodiments be higher, including saturated. Sodium acetate may alternately be used in the same concentration range.

The intermediate product, i.e. the crude oil produced by the centrifugal separation step 38, is then distilled in step 46 in order to collect cannabis oil. There may be multiple distillation processes, the first of which remove the ethanol and the water, if present, from the intermediate product. In other embodiments, the dehydration step is performed using molecular sieves, which are regenerated in an oven after use.

The distillation is run using a film wipe distillation with VTA™, BR™ or Pope™ distillation equipment, or in a rotary evaporator. In some embodiments, a winterization step is implemented before step 46 in order to remove components other than the cannabinoids from the crude oil.

In some embodiments, after step 46, one or more further distillation steps are carried out to increase the purity of the final product. Indeed, the THC content in the final product depends on the final number of distillation passes.

The overall duration of the process depends mostly on the time taken for the co-solvent removal steps.

In some embodiments, a technique such as a salting-out liquid-liquid extraction with subsequent centrifugal extraction involving other solvents is used instead of step 38 to separate the cannabinoids in the form of crude oil from the filtered mixture. Salting-out the water from the ethanol is achieved using sodium acetate or potassium acetate (other salts that may be used include magnesium sulfate, sodium chloride and potassium chloride), then centrifuging and decanting the top aqueous layer to recover the oil rich pellet, and then further refining the oil as required. Salting out tends to make it easier to separate out the oil by centrifuge. Even without salting out, it is necessary to remove the aqueous layer before distillation. In some embodiments, it is possible to not even salt out and instead, just centrifuge and separate.

In some embodiments, step 34 includes one or more further filtration steps. For example, a membrane filtration with a pore size of 1 to 10 μm or an activated charcoal bed filtration is implemented to remove impurities and fine particles of spent biomass from the filtered mixture.

In some embodiments, step 38 is replaced by one or more further filtration steps. For example, a membrane filtration with a pore size of 1 to 10 μm or an activated charcoal bed filtration is implemented to remove impurities and fine particles of spent biomass from the filtered mixture.

In some embodiments, water and ethanol are removed from the filtered mixture using a rotary evaporator.

D. Exemplary Apparatus

Figure 3:
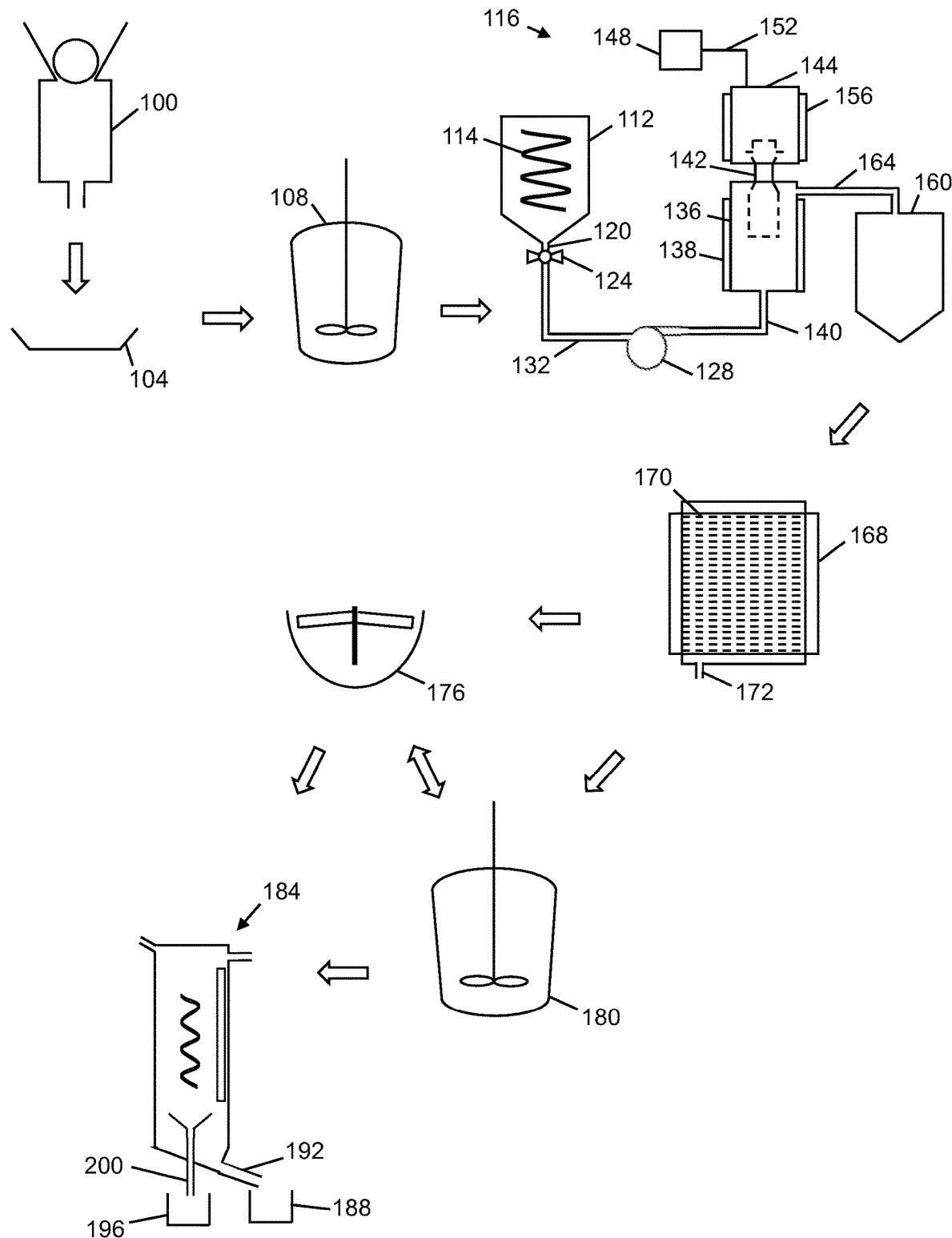
FIG. 3 is a diagram representing the apparatus for extracting cannabinoids from cannabis biomass according to an embodiment of the present invention.

Referring to FIG. 3, cannabis biomass passes through a milling machine 100. Milled cannabis biomass is collected on a tray 104. The milled cannabis biomass is then introduced into a mixing vessel 108. A co-solvent made up of a mixture of water and ethanol is added to the mixing vessel 108. The co-solvent is mixed with the milled cannabis biomass in the mixing vessel 108 to form a slurry.

In some embodiments, the milling machine 100 is mounted in series with the mixing vessel 108 in order to provide for a continuous process. For example, the milled cannabis biomass is directly collected in the mixing vessel 108 via a pipe or chute (not shown) that connects the milling machine 100 and the mixing vessel 108.

After that, the slurry is added to a first vessel 112 of the ultrasonication apparatus 116. A flow-through ultrasonicator such as a Sonomechanics ISP3000™, BSP1200™ or LSP500™ is sufficient. The first vessel 112 has a chiller 114 for keeping the slurry cool, i.e. between room temperature (25° C.) and 2° C., with 4° C., for example, being a suitable temperature. The first vessel 112 has an outlet 120 with a valve 124 mounted on it. The outlet 120 is connected to a pump 128 via a pipe 132. The slurry passes through the pipe 132 by opening the valve 124. The pipe 132 is, in some embodiments, thermally insulated to prevent the slurry flowing through it from warming up.

In some embodiments, the first vessel 112 of the ultrasonication apparatus 116 is equipped with an impeller driven by a motor or a gearbox. Therefore, in these embodiments, the mixing vessel 108 is not used because the mixing to form a slurry can be carried out in the first vessel 112.

Then, the slurry is introduced into a flow-through cell unit or cell unit 136 via a pipe 140 connecting the pump 128 to the cell unit. The cell unit 136 is maintained at a temperature between room temperature (25° C.) and 2° C., for example 4° C., with a cooling jacket 138. Other techniques for cooling are used in other embodiments, such as water baths or a jacketed chiller around the hopper 112, pipe 132, pump 128 and cell unit 136.

The slurry in the cell unit 136 is exposed to ultrasound. The ultrasound is provided in the cell unit 136 by an ultrasonic probe or ultrasonic horn 142. In some embodiments, the ultrasonic horn 142 is a barbell-shaped ultrasonic horn. The ultrasonic horn 142 is driven by a transducer 144. In some embodiments, ultrasound is applied to the slurry with a different ultrasonic setup.

The transducer 144 is connected to a generator 148 via a cable 152. The generator 148 generates a vibration profile that triggers a periodic displacement of the ultrasonic horn 142 according to the profile. The displacement of the ultrasonic horn 142 in the cell unit 136 is responsible for the generation of ultrasound. This ultrasound facilitates the extraction of the cannabinoids from cannabis biomass in the slurry.

The transducer 144 is prevented from overheating using a cooling system such as a cooling jacket 156. In some embodiments, a different type of cooling system is implemented. A continuous vibration profile may be applied to the transducer 144 since the transducer 144 has the cooling jacket 156 to prevent it from overheating. As a result, the extraction of the cannabinoids from the slurry in the cell unit 136 is continuous. Optionally, a booster may be added between the transducer 144 and the cell unit 136.

The slurry is carried out from the cell unit 136 into a second vessel 160 via a pipe 164.

Then, the slurry is passed through a filtration device 168 in order to remove the biomass particles and to leave a filtered mixture. The slurry passes through a mesh 170 with a pore size below 2 mm. In some embodiments, the pore size of the mesh 170 is between 0.25 and 0.5 mm. In some embodiments, the mesh 170 is made of nylon or stainless-steel. The filtered mixture is collected from the filtration device 168 via an outlet 172 located at the bottom part of the filtration device. In some embodiments, the filtration device 168 is a mesh 170 mounted on a container. The mesh 170 retains the biomass particles while the container collects the filtered mixture. The mesh 170 is periodically removed, cleaned, and replaced during the process.

In some embodiments, the outlet 172 drains into a container (not shown) that is periodically removed, emptied, and replaced during the process.

In some embodiments, the mesh 170 is directly mounted in the second vessel 160 of the ultrasonication apparatus 116. This configuration allows this portion of the process to be implemented continuously. In addition, the duration of the process is shorter when continuous.

In some cases, the filtration device 168 is used for an additional filtration step, or multiple filtration devices are used.

In one embodiment, the filtered mixture is then carried into a centrifuge 176 to separate the cannabinoids in the form of crude oil from the filtered mixture.

In another embodiment, the filtered mixture is placed in a mixing vessel 180. Potassium acetate is then added to the mixing vessel 180 and mixed with the filtered mixture in the mixing vessel 180.

In another embodiment, the filtered mixture is carried into the centrifuge 176 just to remove the remaining, finer solid particulates from the filtered mixture. The resulting crude oil dissolved in co-solvent is then placed in a mixing vessel 180. Potassium acetate is then added to the mixing vessel 180 and mixed with the crude oil dissolved in co-solvent in the mixing vessel 180.

After centrifuging, the intermediate product from the prior step (i.e. crude oil) is winterized and then distilled via a short-path film wipe distillation device 184. Since we are using a wiped film distillation process versus a conventional short path still apparatus it is important to have separated the waxes, fats and lipids pre-distillation, which may be achieved using additional filtering or treatment steps as required. If this is not done, the waxes, fats and lipids will be wiped onto the wipe film causing the distillation of some of these elements into the final product. In some embodiments, a different distillation setup is used.

The crude oil is run through the short-path distillation film wipe apparatus 184 to remove some volatile terpenes, for example. The cannabis oil is collected in a vial 188 via a residue discharge arm 192 from the short-path distillation film wipe apparatus 184 while the volatile terpenes are collected in another vial 196 via the distillate discharge arm 200. The number of runs through the short-path distillation film wipe apparatus 184 depends on the targeted purity of the final product.

E. Example

In a specific example, 100 g of cannabis flower is milled using a Magic Bullet™ grinder to produce a cannabis material with a particle size<2 mm. The milled cannabis is added to 1500 mL of pre-chilled (10° C.) co-solvent with a composition of 95% water and 5% ethanol by volume in a 4 L beaker. The cannabis and co-solvent are mixed with an overhead mechanical stirrer, set at 400 RPM for 5 minutes. The resulting slurry is poured into a reservoir, which is connected to the flow through ultrasonicator device with a circulating pump and a 25 mm (1") hose. The ultrasonicator transducer is automatically cooled by a chiller (operating at 10 L/min at a temperature at or below 10° C.), which is set to continuous operation during the flow through of the slurry. A 25 mm (1") tube at the other end of the flow through ultrasonicator device is routed to a nylon mesh over a beaker to collect the liquid and separate the biomass.

The slurry is flowed through the ultrasonicator device at a rate of 1 L/min, with settings on the ultrasonicator as follows: 2000 W power, 100% amplitude, 20 kHz. The pump and ultrasonicator are turned off when batch is completely through. The biomass material is recovered and retained for testing of remaining cannabinoids for re-flow through if necessary. The liquid that is separated from the biomass is centrifuged at 1500 RPM to separate solids, and then decanted to remove the oil-rich layer from the top of centrifuge tube. Note that in some cases, the oil may be part of the pellet or bottom layer, depending on density; if the oil is pure enough it will have a density>1 g/ml. In these cases, separation of the oil from the solids in the pellet will be required.

Depending on requirements, the oil-rich layer is subjected to rotary evaporation or further treatment and/or distillation as desired.

F. Variations

In some embodiments, providing that the co-solvent is kept cool throughout the process, it is possible to increase the proportion of ethanol in the co-solvent mixture. For example, a 10% ethanol and 90% water co-solvent has a flash point of 49° C. (120° F.) and may be used as long as the mixture is kept cooled well below the flash point. In other embodiments, a 20% ethanol and 80% water co-solvent may be used if the mixture is kept well below the flashpoint of 36° C. (97° F.). Providing that the co-solvent and mixture are maintained below room temperature (i.e. <25° C.), and depending on how cool the co-solvent and mixture are kept, the co-solvent may be composed of 5-20% ethanol and the remainder water.

In some embodiments, different techniques are used for the recovery of oil from the co-solvent. For example, after filtering the slurry in step 34, 3A size molecular sieves may be used as a solid stationary phase to separate the oil from water, in a column chromatography process. The filtered mixture is passed through the sieves as the eluent to dehydrate it, resulting in an oil rich ethanol eluate. Depending on the embodiment, centrifuging may be performed before or after passing the filtered mixture through the molecular sieves.

As another example, silica or alumina may be used as a solid column material in a column chromatography process to separate the compounds in the filtered mixture, based on polarity and/or hydrophobicity. In general, reverse phase chromatography may be used, in which the water elutes first, and the less polar oils and/or cannabinoids elute later. Depending on the embodiment, centrifuging may be performed before or after passing the filtered mixture through the solid column.

Another method is to use liquid separation based on liquid/liquid extraction, using a nonpolar solvent such as hexane or heptane to preferentially attract the cannabinoids from the co-solvent. Using a separatory funnel, for example, to separate the organic and aqueous layer, the organic layer may be removed from the co-solvent by evaporation or distillation using a rotary evaporator, falling film evaporator, or VTA™ or BR™ distillation equipment. The organic layer may then be further refined as required. While this may now create a flammable concentrate, the amount of flammable solvent used is less than the amount that would be used in a pure ethanol extraction. A further advantage of this method is that by using 95% water and 5% ethanol as the co-solvent to do the first extraction, one extracts fewer impurities, e.g. wax, pigments, fat, than using pure ethanol as the extraction solvent. Note that, traditionally, pure ethanol extraction processes need to be cold or include a winterization step to achieve low impurity extraction levels. Also, via the second pass of using a non-polar solvent, a rich oil with a high purity of cannabinoids results, which saves considerable purification effort. In other embodiments, the organic and aqueous layers are separated using a centrifuge, and the cannabinoid rich oil in the immiscible solvent (i.e. heptane or pentane) is collected and distilled.

Various components of the apparatus may be connected to each other. Alternatives for the final distillation process include spinning band, wiped film and chromatography.

Throughout the description, specific details have been set forth in order to provide a more thorough understanding of the invention. However, the invention may be practiced without these particulars. In other instances, well known elements have not been shown or described in detail and repetitions of steps and features have been omitted to avoid unnecessarily obscuring the invention. For example, various pumps, valves, jackets and lines are not shown for clarity. Accordingly, the specification and drawings are to be regarded in an illustrative, rather than a restrictive, sense.

In general, unless otherwise indicated, singular elements may be in the plural and vice versa with no loss of generality. Temperatures that have been given to the nearest degree include all temperatures within a range of ±0.5° C. of the given value. Numbers are to be understood to be to the nearest last significant figure.

It will be clear to one having skill in the art that further variations to the specific details disclosed herein can be made, resulting in other embodiments that are within the scope of the invention disclosed. Steps in the flowchart may be performed in a different order, other steps may be added, or one or more may be removed without altering the main outcome of the process. All parameters, dimensions, materials, and configurations described with respect to a specific embodiment are examples only and may be changed depending on the specific embodiment. Accordingly, the scope of the invention is to be construed in accordance with the substance defined by the following claims.

The invention claimed is:

1. A process for extracting tetrahydrocannabinol, cannabidiol, or both from cannabis consisting essentially of:
   a) mixing a co-solvent consisting essentially of 95-97% water and 3-5% ethanol by volume with cannabis to form a slurry;
   b) applying ultrasound to the slurry to extract cannabinoids from the cannabis into the co-solvent;
   c) filtering the slurry to remove solid particles from the slurry to form a filtered mixture;
   d) centrifuging the filtered mixture to remove solid particles from the centrifuged filtered mixture;
   e) adding potassium acetate to the centrifuged filtered mixture in order to break a water/ethanol azeotrope in the centrifuged filtered mixture; and
   f) distilling the centrifuged filtered mixture to remove the ethanol and the water with a distillation apparatus to yield tetrahydrocannabinol, cannabidiol, or both from cannabis.

2. The process of claim 1, wherein the co-solvent has a flash point above 62° C.

3. The process of claim 1, further milling the cannabis to a particle size below 2 mm.

4. The process of claim 1, wherein the slurry is filtered using a mesh bag with a pore size below 2 mm.

5. The process of claim 4, wherein the mesh bag has a pore size of 0.25-0.5 mm.

6. The process of claim 4, wherein:
the mixing step occurs in a first vessel of an ultrasonication apparatus;
a flow of the slurry between the first vessel and a second vessel of the ultrasonication apparatus is continuous; and
the mesh bag is set in the second vessel.

7. The process of claim 1, further filtering the centrifuged filtered mixture through a membrane filter with a pore size of 1 to 10 μm.

8. The process of claim 1, wherein the distillation apparatus is a film wipe distillation apparatus.

\* \* \* \* \*